United States Patent
Edwards

(10) Patent No.: US 7,141,539 B2
(45) Date of Patent: Nov. 28, 2006

(54) PROCESS FOR PRODUCING DETERGENT MOLECULES COMPRISING AN ETHER LINKAGE FROM BUTADIENE

(75) Inventor: Charles Lee Edwards, Houston, TX (US)

(73) Assignee: Shell Oil Company, Houston, TX (US)

(*) Notice: Subject to any disclaimer, the term of this patent is extended or adjusted under 35 U.S.C. 154(b) by 340 days.

(21) Appl. No.: 10/887,736

(22) Filed: Jul. 9, 2004

(65) Prior Publication Data

US 2005/0037940 A1 Feb. 17, 2005

Related U.S. Application Data

(60) Provisional application No. 60/494,205, filed on Aug. 11, 2003.

(51) Int. Cl.
*C11D 1/722* (2006.01)
*C07C 41/06* (2006.01)

(52) U.S. Cl. .................................. 510/506; 568/613
(58) Field of Classification Search ................... None
See application file for complete search history.

(56) References Cited

U.S. PATENT DOCUMENTS

| | | | |
|---|---|---|---|
| 4,180,694 A | 12/1979 | Nozaki | 585/511 |
| 4,229,605 A | 10/1980 | Nozaki | 585/509 |
| 4,229,606 A | 10/1980 | Nozaki | 585/509 |
| 4,687,876 A | 8/1987 | Nozaki | 585/509 |
| 5,030,792 A | 7/1991 | Slaugh | 585/639 |
| 5,412,137 A | 5/1995 | Prashad et al. | 558/146 |

FOREIGN PATENT DOCUMENTS

| | | |
|---|---|---|
| EP | 0218100 A1 | 4/1987 |
| EP | 0278407 A2 | 8/1988 |
| EP | 1178029 A1 | 2/2002 |
| GB | 2114974 A | 9/1983 |
| WO | 90/13531 | 11/1990 |
| WO | WO 92/10450 | 6/1992 |
| WO | WO 93/02032 * | 2/1993 |
| WO | 94/14822 | 7/1994 |
| WO | 02/062732 A1 | 8/2002 |

OTHER PUBLICATIONS

R. Patrini et al., Journal of Molecular Catalysis A: chemical 129 (1998) 179-189. Mar., 1998.*
"Palladium-catalyzed telomerization of butadiene with ethylene glycol in liquid single phase and biphasic systems: control of selectivity and catalyst recycling" by Arno Behr, Michael Urschey, *Journal of Molecular Catalysis A, Chemical*, vol. 197 (Apr. 18, 2003) pp. 101-113.
"Sex Pheromones of Summerfruit Tortrix Moth, Adoxophyes Orana 2. Compounds Influencing Their Attractant Activity" by S. Voerman and A. K. Minks, *Environmental Entomology, Entomological Society of America*, vol. 2, No. 5, (Oct. 15, 1973)pp. 750-756.
"Allylation Using Allylborates" by Roger Hunter, *Tetrahedron*, Elsevier Science Publishers, Amsterdam, Netherlands, vol. 50, No. 3, (1994) pp. 871-888.
International Search Report of Feb. 23, 2005.
Written Opinion for PCT/US2004/025815 dated Feb. 23, 2005.
International Preliminary Examination Report on Patentability for PCT/US2004/025815 of Sep. 12, 2005.
International Search Report of Feb. 18, 2004.
Written Opinion of PCT/US2004/025814 of Feb. 18, 2004.

* cited by examiner

*Primary Examiner*—John R. Hardee

(57) ABSTRACT

Novel detergent molecules and methods for producing such detergent molecules by dimerizing and alkoxylating butadiene with one or more reactant alkanol selected from the group consisting of a primary alkanol and an $\alpha, \omega$-diol, hydrogenating the alkoxydimerization product to produce a hydrogenation product selected from the group consisting of primarily 1-alkoxy substituted 2-octene and primarily 1-hydroxy-alkoxyoctane, and hydroxylating the 1-alkoxy substituted 2-octene to produce primarily 1-hydroxy-9-alkoxy nonanes.

95 Claims, No Drawings

PROCESS FOR PRODUCING DETERGENT MOLECULES COMPRISING AN ETHER LINKAGE FROM BUTADIENE

This application claims the benefit of U.S. Provisional Application No. 60/494,205 filed Aug. 11, 2003, the entire disclosure of which is hereby incorporated by reference.

FIELD

The application relates to detergent molecules comprising an ether linkage which increases cold water solubility, and to processes for making same.

BACKGROUND

Detergent alcohols generally have been made by oligomerizing ethylene to produce olefins having a desired number of carbon atoms, and then producing a primary detergent range alcohol from the resulting olefins. The detergent range alcohols are produced by a number of commercial processes, such as by oxo or hydroformylation of long chain olefins. Unfortunately, ethylene is a relatively expensive starting material. In addition, preparation of long chain olefins by olefin oligomerization is not amenable to fine tuning to produce only those olefins or alcohols demanded by clients.

Methods for producing a controllable slate of detergent molecules are needed which do not necessarily rely on ethylene as a starting material.

BRIEF SUMMARY

The application provides a method for producing detergent molecules from butadiene. The method comprises:

dimerizing and alkoxylating butadiene with one or more reactant alkanols selected from the group consisting of a primary alkanol and an $\alpha$, $\omega$-diol, the dimerizing and alkoxylating occurring in the presence of one or more alkoxy substituted phosphine ligands under alkoxydimerization conditions comprising an alkoxydimerization catalyst, the alkoxydimerization conditions being effective to produce an alkoxydimerization product comprising one or more octadienes selected from the group consisting of primarily 1-alkoxy-2,7-octadienes where the reactant alkanol is a primary alkanol and 1-hydroxyalkoxy-2,7-octadienes wherein the reactant alkanol is an $\alpha$, $\omega$-diol;

hydrogenating the alkoxydimerization product under hydrogenation conditions comprising a hydrogenation catalyst, the hydrogenation conditions being effective to produce a hydrogenation product selected from the group consisting of primarily 1-alkoxy substituted 2-octene and primarily 1-hydroxy-alkoxyoctane, respectively; and, when the hydrogenation product is primarily 1-alkoxy substituted 2-octene, hydroxylating the 1-alkoxy substituted 2-octene under hydroxylation conditions effective to produce primarily 1-hydroxy-9-alkoxy nonanes.

DETAILED DESCRIPTION

The present application uses butadiene as a starting material in a process which uses addition reactions, rather than chain growth reactions, to produce detergent molecules. Butadiene is less expensive than ethylene, and its use as a starting material renders the process economically attractive. In addition, the process can be fine tuned to produce only specific alcohols.

Primary alcohols of olefins having from about 6 to about 36 carbon atoms, preferably from about 6 to about 33 carbon atoms, have commercial importance as detergents, soaps, surfactants, and freeze point depressants in lubricating oils. Primary alcohols having from about 8 to about 18 carbon atoms are in particular demand. The present application provides a process which is effective to make a variety of primary alcohols having from about 10 to about 15 carbon atoms. The resulting primary alcohols also comprise an ether linkage in the hydrophobe, which advantageously imparts increased cold water solubility to the detergent molecules compared to fatty alcohols having a similar carbon number.

The resulting detergent molecules have a structure selected from the group consisting of:

R—O—CH$_2$(CH$_2$)$_7$CH$_2$OH, wherein R is an alkyl group having substantially any number of carbon atoms effective to produce desired detergency and cold water solubility characteristics, preferably from about 1 to about 6 carbon atoms. These detergent molecules also are referred herein to 1-hydroxy-9-alkoxy nonanes; and CH$_3$(CH$_2$)$_7$OCH$_2$(CH$_2$)$_x$OH, wherein x is from 1 to 3, preferably 2 or 3. These detergent molecules also are referred to herein as 1-hydroxyalkoxy-octanes.

The structure of the final detergent molecules depends upon the alkanol chosen to alkoxylate the butadiene. Suitable "reactant alkanols" are selected from the group consisting of a primary alkanols and $\alpha$, $\omega$-diols. Where the reactant alkanol is a primary alkanol, the final product has the structure R—O—CH$_2$(CH$_2$)$_7$CH$_2$OH, referred to as 1-hydroxy-9-alkoxy nonanes. When the reactant alkanol is an $\alpha$, $\omega$-diol, the final product has the structure CH$_3$(CH$_2$)$_7$OCH$_2$(CH$_2$)$_x$OH, referred to as 1-hydroxyalkoxy-octanes.

In order to produce the foregoing detergent molecules, two moles of butadiene are reacted with the reactant alkanol or diol by a process called "alkoxydimerization" to produce (a) 1-alkoxy-2,7-octadiene compounds, when a primary alkanol is the reactant alkanol, or (b) 1-hydroxyalkoxy-2,7-octadiene compounds, when an $\alpha,\omega$-diol is the reactant alkanol. Selective hydrogenation of the 1-alkoxy-2,7-octadiene compounds produces 1-alkoxy-2-octene compounds, which are hydroformylated to produce 1-hydroxy-9-alkoxy nonanes containing an ether linkage nine atoms removed from the primary hydroxyl group. Complete hydrogenation of the 1-hydroxyalkoxy-2,7-octadienes produces 1-hydoxy-alkoxyoctane.

The general reaction using a primary alkanol as the reactant alkanol is shown below:

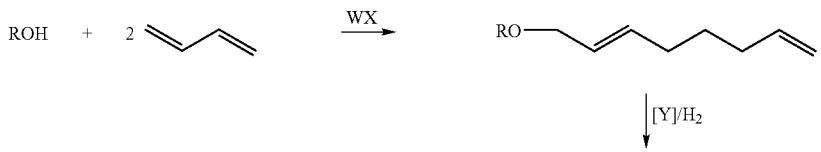

-continued

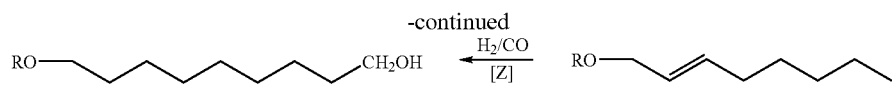

wherein
R is selected from the group consisting of alkyl groups having from about 1 to about 6 carbon atoms;
W is an alkoxydimerization catalyst comprising a noble metal;
X is an alkoxy substituted phosphine ligand;
Y is a hydrogenation catalyst comprising one or more metals; and,
Z is a hydroformylation catalyst.
Where the reactant alkanol is an α, ω-diol, the reaction is as follows:

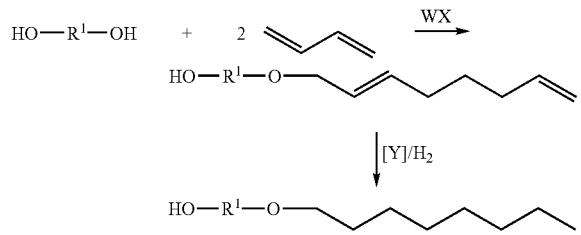

wherein
$R^1$ is selected from the group consisting of alkylene groups having from about 2 to about 4 carbon atoms, preferably from 3 to 4 carbon atoms;
W is an alkoxydimerization catalyst comprising a noble metal;
X is an alkoxy substituted phosphine ligand;
Y is a hydrogenation catalyst comprising one or more metals;
Z is a hydroformylation catalyst.

Combined Dimerization and Alkoxy-Substitution of the Butadiene to Produce Alkoxy Substituted Octadienes The dimerization and alkoxy-substitution of the butadiene occur during the same reaction, herein called the "alkoxydimerization process." In order to perform the alkoxydimerization process, the reactant alkanol, the alkoxydimerization catalyst, and the butadiene are mixed. It is possible to mix the butadiene with the reactant alkanol and thereafter to add the ligand(s) discussed below. However, it is preferable to add the ligand(s) to the reactant alkanol, to mix the alkoxydimerization catalyst with the resulting alkanol/ligand solution, to activate the catalyst, and then to add the butadiene.

Suitable reactant alkanols are selected from the group consisting of primary alkanols and α-,ω-diols. Preferred primary alkanols have from about 1 to about 6 carbon atoms. Preferred α-,ω-diols have from about 2 to about 4 carbon atoms, preferably from 3 to 4 carbon atoms. The reactant alkanol serves as a solvent and a reactant in the alkoxydimerization reaction.

Suitable ligands are effective to promote the formation of a product comprising primarily the 1-alkoxy or the 1-hydroxyalkoxy-substituted octadiene, respectively. For convenience, 1-alkoxy substituted and 1-hydroxyalkoxy substituted are collectively referred to as "1-alkoxy substituted" molecules. In a preferred embodiment, the ligands are effective to form a product comprising 90 wt. % or more of the 1-alkoxy substituted octadiene, preferably greater than 90 wt. % of the 1-alkoxy substituted octadiene, more preferably greater than 93 wt. % of the 1-alkoxy substituted octadiene, and most preferably 95 wt. % or more of the 1-alkoxy substituted octadiene. In a most preferred embodiment, the ligands also are effective to stabilize the catalyst. This is evidenced by a reduction in (or the absence of) deposition of noble metal onto the reactor walls during the reaction when compared to the same reaction performed in the absence of the ligand. The quantity of ligand preferably is from about 0.8 moles to about 1.2 moles.

Preferred ligands include, but are not necessarily limited to alkoxy substituted phosphine ligands, preferably alkoxy substituted phenyl phosphine ligands. Alkoxy substituted phenyl phosphine ligands are effective to prevent decomposition of the alkoxydimerization catalyst. Preferred alkoxy substituted phenyl phosphine ligands include, but are not necessarily limited to tris-(2,4,6,trimethoxy phenyl)phosphine and tris-(4-methoxyphenyl)phosphine. A most preferred ligand is tris-(4-methoxyphenyl)phosphine.

The reactant alkanol and the ligands are mixed using any suitable conditions to produce an alkanol/ligand solution. Preferably, the ligands are added to the reactant alkanol and the mixture is agitated.

In a preferred embodiment, the alkoxydimerization catalyst is mixed with the alkanol/ligand solution to produce an alkoxydimerization catalyst mixture. The alkoxydimerization catalyst comprises a noble metal. Suitable noble metals for the alkoxydimerization catalyst include but are not necessary limited to platinum, palladium, iridium, rhenium, ruthenium, and osmium. Preferred noble metals include, but are not necessarily limited to palladium, platinum, and ruthenium. A most preferred noble metal for the alkoxydimerization catalyst is palladium.

The alkoxydimerization catalyst preferably is a salt of a noble metal. The noble metal salt may be soluble or superficially insoluble in the reactant alkanol or alkanol/ligand mixture. By "superficially insoluble" is meant that the alkoxydimerization catalyst comprises salt(s) which appear to be insoluble in the reactant alkanol or alkanol/ligand mixture, but which apparently produce "noble metal moieties" which are catalytically effective.

Without being bound by any particular theory unless claimed, the chemical transformations that involve the alkoxydimerization catalyst are quite complex, probably involving the formation and destruction of complexes between the noble metal salt or noble metal moieties, the butadiene, and/or the presumed butadiene dimer intermediate. The formation of catalytically effective noble metal moieties is believed to be influenced by interaction of the alkoxydimerization catalyst with the butadiene, the presumed butadiene dimers, and/or the reactant alkanol. To obtain optimum reaction rates, the alkoxydimerization catalyst preferably is an alkanol-soluble noble metal salt.

Suitable salts of the noble metal are organic or inorganic acids. Illustrative examples include the halide and oxalate salts. Also suitable are salts wherein the metal is present in the anion as, for example, chloropalladate salt or chloroplatinate salts. Metal complexes also are suitable, such as metal complexes with tertiary nitrogen-containing ligands.

The known τ-allyl complexes are also suitably used. Most preferred alkoxydimerization catalysts comprises two noble metal atoms per molecule. Such alkoxydimerization catalysts include, but are not necessarily limited to tris(dibenzylideneacetone)di noble metal. A preferred alkoxydimerization catalyst is tris(dibenzylideneacetone)dipalladium. The alkoxydimerization catalyst may be provided fresh and/or as a recycled stream from the alkoxydimerization (or telomerization) process.

Only catalytic quantities of the noble metal are required. Although a larger amount of alkoxydimerization catalyst is not detrimental to the process, the amount used generally is sufficient to produce an alkoxydimerization catalyst mixture comprising from about 0.005% mole to about 0.1% mole noble metal, based on total reactants, preferably from about 0.01% mole to about 0.05% mole noble metal.

The alkoxydimerization catalyst mixture is exposed to "activation conditions" effective (a) to dissolve reactants other than the alkoxydimerization catalyst, and (b) to activate the alkoxydimerization catalyst. The result is an "activated catalyst mixture." The activation conditions comprise maintaining the alkoxydimerization catalyst mixture at an "activation temperature" for a period of time effective to activate the catalyst (referred to as the "activation time"). If the alkoxydimerization catalyst is an alkanol soluble noble metal salt, then the activation temperature and the activation time are effective to dissolve the noble metal salt in the alkanol/ligand solution. If the alkoxydimerization catalyst is superficially alkanol insoluble, then the activation temperature and activation time are effective to liberate "noble metal compound moieties" in the alkanol/ligand solution.

A suitable activation temperature is about 0° C. or more, preferably about 25° C. The activation time preferably is as short as possible, limited primarily by practical constraints. A suitable activation time is about 1 minute or more. A preferred activation time is about 10 minutes. The method of mixing is not critical, although some agitation decreases the activation time.

Butadiene preferably is added to the activated catalyst mixture. The butadiene may be obtained from any known source. The amount of butadiene added is effective to produce an optimum butadiene:alkanol mole ratio. The optimum butadiene:alkanol mole ratio depends in part upon the specific reactant alkanol and the desired conversion. A butadiene:alkanol mole ratio of as low as about 1:5 is suitable if low conversion is desired. To obtain higher conversion, a more substantial proportion of butadiene is preferred and the butadiene:alkanol mole ratio is from about 1:3 to about 1:0.5. Best results are obtained when the butadiene:alkanol mole ratio is from about 1:2 to about 1:1.

It is possible to use other solvents in the reaction mixture as long as those solvents are inert to the reactants. However, the use of additional solvent other than the reactant alkanol is not preferred. If another solvent is deemed advisable, suitable solvents are those listed below as suitable for hydrogenation.

In a preferred embodiment, butadiene is added to the activated catalyst mixture. Because the addition of butadiene to the activated catalyst mixture generally produces an exothermic reaction, the activated catalyst mixture preferably is cooled to a preliminary temperature sufficiently low to control the exothermic reaction. The butadiene is added to this cooled activated catalyst mixture. Preferably, the temperature of the cooled activated catalyst mixture is about 0° C. or less, preferably to about −60° C. The butadiene-containing cooled activated catalyst mixture is the "final alkoxydimerization mixture."

The final alkoxydimerization mixture is slowly heated to a preliminary temperature of about 60° C. or less, preferably about 25° C. or less, preferably with agitation. Thereafter, the final alkoxydimerization mixture is heated to and maintained at an alkoxydimerization temperature effective to produce about 90 wt. % or more of the 1-alkoxy substituted octadiene. A preferred alkoxydimerization temperature is about 60° C. The alkoxydimerization temperature is maintained for an alkoxydimerization time of about 2 hours or more, preferably about 8 hours or less, more preferably about 6 hours or less, most preferably about 4 hours.

Typical alkoxydimerization pressures vary from about 5 atmospheres to about 20 atmospheres. Frequently, good results are obtained when the alkoxydimerization pressure is autogenous, or when the alkoxydimerization pressure is the pressure generated when the reactants are maintained at the alkoxydimerization temperature in a sealed reaction vessel. Such pressures are from about 1 atmosphere to about 20 atmospheres.

Once the alkoxydimerization time has passed, the final alkoxydimerization mixture is cooled, preferably to the preliminary temperature, most preferably to about 25° C. or less. The cooled final alkoxydimerization product is depressurized. The cooled final alkoxydimerization product may be fed directly to hydrogenation, or the alkoxylated octadienes may be recovered and fed to hydrogenation. Recovery of the alkoxylated octadienes is accomplished using any suitable conventional means, such as selective extraction, fractional distillation and chromatographic techniques.

In a preferred embodiment, the yield of the desired 1-alkoxy substituted octadiene is 90 wt. % or more, preferably greater than 90 wt. %, more preferably greater than 93 wt. %, and most preferably 95 wt. % or more.

Hydrogenation

Depending upon the identity of the reactant alkanol, the alkoxydimerization product is either fully hydrogenated to a saturated alcohol or selectively hydrogenated.

Because the alkoxydimerization catalyst comprises a noble metal, it is possible to perform the hydrogenation using the alkoxydimerization catalyst. However, greater efficiency is achieved when the alkoxydimerization product is separated and fed to a hydrogenation reactor comprising a fixed bed hydrogenation catalyst. Substantially any of the known heterogeneous or homogeneous hydrogenation catalysts may be used. Preferred hydrogenation catalysts are heterogeneous hydrogenation catalysts.

Suitable hydrogenation catalysts comprise a metal having an atomic number of from 26 to 78, which includes but is not necessarily limited to Fe, Co, Ni, Cu, Zn, Ga, Ge, As, Se, Br, Kr, Rb, Sr, Y, Zr, Nb, Mo, Tc, Ru, Rh, Pd, Ag, Cd, In, Sn, Sb, Te, I, Xe, Cs, Ba, the lanthanide series (comprising Ce, Pr, Nd, Pm, Sm, Eu, Gd, Tb, Dy, No, Er, Tm, Yb, Lu), Hf, Ta, W, Re, Os, Ir, Pt. Preferred metals for the hydrogenation catalyst have an atomic number of 28 to 78 [Ni, Cu, Zn, Ga, Ge, As, Se, Br, Kr, Rb, Sr, Y, Zr, Nb, Mo, Tc, Ru, Rh, Pd, Ag, Cd, In, Sn, Sb, Te, I, Xe, Cs, Ba, the lanthanide series (comprising Ce, Pr, Nd, Pm, Sm, Eu, Gd, Tb, Dy, No, Er, Tm, Yb, Lu), Hf, Ta, W, Re, Os, Ir, Pt]. Other known catalysts suitable for hydrogenation include the oxides and sulfides of Group VI, including but not necessarily limited to Cr, Mo and W.

The hydrogen may be provided as pure hydrogen or the hydrogen may be diluted with one or more additional gases. Suitable additional gases are inert, and do not interfere with the hydrogenation process. For example, it may be desirable to use a process gas, such as syngas, to supply the required hydrogen. Such a process gas is suitable for use as the hydrogen source as long as the process gas does not interfere with the hydrogenation process.

The hydrogenation is either a batch process or a continuous process, preferably continuous. In a batch process, a homogeneous or heterogeneous catalyst is charged to the reactor along with the reactants and the reactor is pressured with hydrogen, or a hydrogen-containing gas. In a continuous process the hydrogenation catalyst preferably is a packed bed of solid catalyst, more preferably a supported metal catalyst, and the alkoxy substituted octadienes and hydrogen are simultaneously passed through the bed, which is maintained at hydrogenation conditions.

The hydrogenation is conducted in the presence or absence of a solvent. If a solvent is used, the solvent preferably is inert to the hydrogenation conditions. Suitable solvents include, but are not necessarily limited to ethers, aromatic hydrocarbons, paraffins, halogenated hydrocarbons, and nitriles. Suitable ethers include, but are not necessarily limited to dialkyl ethers, alkyl aryl ethers, cyclic ethers, and lower alkyl ethers. Example of such ethers include, but are not necessarily limited to dibutyl ether, methyl hexyl ether, anisole, phenyl butyl ether, tetrahydrofuran, dioxane, dioxolane, ethylene glycol dimethyl ether, diethylene glycol dimethyl ether, tetraethylene glycol dimethyl ether, and glycol triethyl ether. Suitable aromatic hydrocarbons include, but are not necessarily limited to benzene, toluene, and xylene. Suitable halogenated hydrocarbons include, but are not necessarily limited to chloroform, carbon tetrachloride, tetrachloroethylene, methylene chloride and bromoform. Suitable sulfoxides include, but are not necessarily limited to dimethylsulfoxide. Suitable nitriles include but are not necessarily limited to acetonitrile and benzonitrile.

In a preferred embodiment, the alkoxy substituted octadienes and hydrogen are simultaneously passed through a bed of supported metal catalyst which is maintained at hydrogenation conditions, described below.

Complete Hydrogenation of
1-hydroxyalkoxy-2,7-octadiene

Where the reactant alkanol is a diol, the hydrogenation conditions are effective to completely hydrogenate 1-hydroxyalkoxy-2,7-octadiene. The reactor is maintained at complete hydrogenation conditions for a complete hydrogenation time effective to completely hydrogenate the alkoxy substituted octadienes and to produce primarily 1-hydroxyalkoxyoctanes.

Complete hydrogenation conditions comprise: an excess of hydrogen based on moles of octadiene; a complete hydrogenation temperature effective to produce complete hydrogenation, suitable complete hydrogenation temperatures generally being from about 30° C. to about 100° C., preferably about 50° C.; a complete hydrogenation time effective to produce complete hydrogenation, suitable complete hydrogenation times generally being about 4 hours or less, preferably about 1 hour; and, a complete hydrogenation pressure effective to produce complete hydrogenation, suitable pressures generally being from about 10 bar to about 15 bar.

Selective Hydrogenation of 1-alkoxy Substituted Octadiene

Where the reactant alkanol is a primary alkanol, the hydrogenation conditions are effective to selectively hydrogenate the 1-alkoxy substituted octadiene to produce 1-alkoxy substituted 2-octene, which is then hydroxylated, preferably by hydroformylation, to produce a primary alcohol.

The reactor is maintained at selective hydrogenation conditions comprising a selective hydrogenation temperature, a selective hydrogenation time, and a selective hydrogen concentration. The selective hydrogenation conditions are effective to selectively hydrogenate the alkoxy substituted octadienes and to produce primarily 1-alkoxy-2-octenes. Selective hydrogenation temperatures generally are from about 0° C. to about 100° C., preferably about 25° C. The selective hydrogenation time generally is about 4 hours, preferably about 1 hour. The selective hydrogen concentration is a molar ratio of hydrogen:octadiene of from about 1:1 to about 1.05:1. Typical hydrogenation pressures are from about atmospheric pressure to about 10 bar or higher.

Careful control over the molar ratio of hydrogen to alkoxy octadiene and the reaction temperature and pressure within the foregoing ranges prevents overhydrogenation and produces selective hydrogenation of the terminal unsaturated carbon-carbon bond of 1-alkoxy-2,7-octadiene to the 1-alkoxy-2-octene.

Hydroformylation

The 1-alkoxy-2-octene produced by selective hydrogenation is converted to a primary alcohol using any suitable procedure. A preferred procedure is hydroformylation.

Hydroformylation is a term used in the art to denote the reaction of an olefin with CO and $H_2$ to produce an aldehyde/alcohol which has one more carbon atom than the reactant olefin. Frequently, the term hydroformylation is used to cover the aldehyde and the reduction to the alcohol step in total, i.e., hydroformylation refers to the production of alcohols from olefins via carbonylation and an aldehyde reduction process. As used herein, hydroformylation refers to the ultimate production of alcohols.

Illustrative hydroformylation catalysts include, but are not necessarily limited to, cobalt hydrocarbonyl catalysts and metal-phosphine ligands comprising metals including, but not necessarily limited to palladium, cobalt, and rhodium. The choice of catalysts determines the various reaction conditions imposed. In a preferred embodiment, the catalyst is cobalt with modified phosphine ligands. One of ordinary skill in the art, by referring to any of the well-known literature on oxo alcohols, can readily determine the conditions of temperature and pressure that will be needed to hydroformylate the olefins. An example in addition to U.S. Pat. No. 5,849,960 is EP 0 903 333 A1, incorporated herein by reference.

Conventional methods of obtaining detergent alcohols generally produce mixtures of alcohols. In these conventional processes, the entire product slate generally must be balanced in order to optimize profitability. In contrast, the present process can be used to produce a single carbon number product or a product comprising a blend of carbon numbers, depending upon market requirements. Whether a single carbon number product or a blend is produced is determined by the identity of the reactant alkanol used in the alkoxydimerization. The following Table summarizes the products that are obtainable by the process using primary alkanols having from 1 to 6 carbon atoms:

| Desired Alcohol | Reactants | Product Structure (a) |
|---|---|---|
| $C_{11}OH$ | $CH_3OH$ + 2 BD + $H_2/CO$ | $CH_3O(CH_2)_8CH_2OH$ |
| $C_{12}OH$ | EtOH + 2 BD + $H_2/CO$ | $CH_3CH_2O(CH_2)_8CH_2OH$ |
| $C_{13}OH$ | n PrOH + 2 BD + $H_2/CO$ | $CH_3CH_2CH_2O(CH_2)_8CH_2OH$ |
| $C_{14}OH$ | n BuOH + 2 BD + $H_2/CO$ | $CH_3CH_2CH_2CH_2O(CH_2)_8CH_2OH$ |
| $C_{15}OH$ | n $C_5OH$ + 2 BD + $H_2/CO$ | $CH_3(CH_2)_4O(CH_2)_8CH_2OH$ |
| $C_{16}OH$ | n $C_6OH$ + 2 BD + $H_2/CO$ | $CH_3(CH_2)_5O(CH_2)_8CH_2OH$ |

(a) The oxygen is counted as a carbon atom.

Unusual blends could be produced, for example, using a single step reaction. For example, a one step alkoxydimerization/hydroformylation in which methanol and butanol were charged to the reactor system would produce 50% of a $C_{10}$ type alcohol having 11 atoms in the chain (1-hydroxy-9-methoxynonane) and 50% of a $C_{13}$ type alcohol having 14 atoms in the chain (1-hydroxy-9-butoxynonane), as shown in the following reaction:

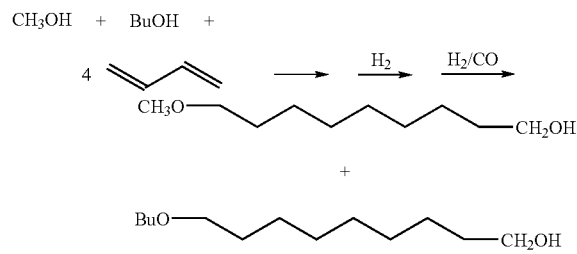

Persons of ordinary skill in the art will recognize that other blends could be made by substituting other combinations of reactant alkanols.

Ranges and limitations other than those specified herein that perform substantially the same function in substantially the same manner to obtain the same or substantially the same result are within the scope of the specification and the claims.

The process will be illustrated by the following examples, which are provided for illustration only and are not intended to limit the scope of the invention.

Alkoxydilmerization of Butadiene

The parameters and results of the alkoxydimerization experiments are given in the following Table, and the experiments are described in more detail below:

EXAMPLE 1

A total of 0.26 grams (0.00028 moles) of tris(dibenzylideneacetone) dipalladium and 0.1 g (0.00028 moles) of tris(4-methoxyphenyl)phosphine was dissolved in 100 g (3.125 moles) of dry methanol (previously dried over 3Δ molecular sieve) and placed in a 500 ml Zipperclave (316 s.s.) autoclave. The reaction mixture was placed under $N_2$ by evacuation and refilling with $N_2$. The reaction mixture was stirred for 10 minutes at 25° C. in order to dissolve all material. Then the reaction mixture was cooled to −60° C. at which time 100 grams (1.85 moles) of butadiene was transferred to the autoclave from the butadiene feed tank. The reaction mixture was allowed to slowly come to 25° C. with stirring and then heated to 60° C. for 4 hours. Initially, the reaction was exothermic requiring cold water addition to maintain at 60° C. The reaction was cooled to 25° C. and depressured.

The contents were transferred to a separatory funnel and a combination of hexane and water was added. The catalyst was removed by water washing and extraction with salt water. The product mixture was dried over anhydrous sodium sulfate and the product mixture was transferred to a vacuum distillation apparatus. Distillation of the product mixture afforded 114 g of a mixture of two isomers of methoxyoctadienes. $C_{13}$ NMR confirmed the presence of 95% m 1-methoxy-2,7-octadiene and 5% m 3-methoxy-2,7-octadiene. This represents an isolated yield of 83.3% basis theoretical product yield.

EXAMPLE 2

Example 1 was repeated exactly except that 100 grams (2.17 moles) of dry ethanol (previously dried over 3Δ molecular sieve) was used instead of methanol. Isolation of the desired products afforded 88 grams of a mixture of two isomers of ethoxyoctadienes. $C_{13}$ NMR confirmed the presence of 94% m 1-ethoxy-2,7-octadiene and 6% m 3-ethoxy-2,7-octadiene. This represents an isolated yield of 62 % m basis theoretical product yield.

EXAMPLE 3

Example 1 was repeated exactly except that 100 grams (1.67 moles) of dry n-propanol (previously dried over 3Δ molecular sieve) was used instead of methanol. Isolation of the desired products afforded 84 grams of a mixture of two isomers of n-propoxyoctadienes. $C_{13}$ NMR confirmed the presence of 96% m 1-n-propoxy-2,7-octadiene and 4% m 3-n-propoxy-2,7-octadiene. This represents an isolated yield of 54% m basis theoretical product yield.

EXAMPLE 4

Example 1 was repeated exactly except that 100 grams (2.17 moles) of dry n-butanol (previously dried over 3Δ molecular sieve) was used instead of methanol. Isolation of the desired products afforded 66 grams of a mixture of two isomers of n-butoxyoctadienes. $C_{13}$ NMR confirmed the presence of 95% m 1-n-butoxy-2,7-octadiene and 5% m 3-n-butoxy-2,7-octadiene. This represents an isolated yield of 39% m basis theoretical product yield.

EXAMPLE 5

Example 1 was repeated exactly except that 100 grams (2.17 moles) of dry n-pentanol (previously dried over 3Δ molecular sieve) was used instead of methanol. Isolation of the desired products afforded 61 grams of a mixture of two isomers of n-pentoxyoctadienes. $C_{13}$ NMR confirmed the presence of 94% m 1-n-pentoxy-2,7-octadiene and 6% m 3-n-pentoxy-2,7-octadiene. This represents an isolated yield of 34% m basis theoretical product yield.

EXAMPLE 6

Example 1 was repeated exactly except that 100 grams (2.17 moles) of dry n-hexanol (previously dried over 3Δ molecular sieve) was used instead of methanol. Isolation of the desired products afforded 56 grams of a mixture of two isomers of n-hexoxyoctadienes. $C_{13}$ NMR confirmed the presence of 95% m 1-n-hexoxy-2,7-octadiene and 5% m 3-n-hexoxy-2,7-octadiene. This represents an isolated yield of 29% m basis theoretical product yield.

EXAMPLE 7

Example 6 was repeated exactly except that 0.2 grams (0.00056 moles) of tris(4-methoxyphenyl)phosphine was used, and the reaction was allowed to stir at 60° C. for 15 hours. Isolation of the desired products afforded 93 grams of a mixture of two isomers of n-hexoxyoctadienes. $C_{13}$ NMR confirmed the presence of 94% m 1-n-hexoxy-2,7-octadiene and 6% m 3-n-hexoxy-2,7-octadiene. This represents an isolateded yield of 48% m basis theoretical product yield.

The foregoing examples are summarized in the following Table:

| Example | Alcohol Used | Pd$_2$(dba)3 (moles) (b) | 4-MP (b) (moles) | Time hrs | Temp. (C.) | Alkoxy-Octadienes Yield (g)/ % Theory | 1-isomer (% m) (c) | 3-isomer (% m) (c) |
|---|---|---|---|---|---|---|---|---|
| 1 | Methanol | 0.00028 | 0.00028 | 4 | 60 | 114 g (83%) | 95 | 5 |
| 2 | Ethanol | 0.00028 | 0.00028 | 4 | 60 | 88 g (62%) | 94 | 6 |
| 3 | n-Propanol | 0.00028 | 0.00028 | 4 | 60 | 84 g (54%) | 96 | 4 |
| 4 | n-Butanol | 0.00028 | 0.00028 | 4 | 60 | 66 g (39%) | 95 | 5 |
| 5 | n-Pentanol | 0.00028 | 0.00028 | 4 | 60 | 61 g (34%) | 94 | 6 |
| 6 | n-Hexanol | 0.00028 | 0.00028 | 4 | 60 | 56 g (29%) | 95 | 5 |
| 7 | n-Hexanol | 0.00028 | 0.00056 | 15 | 60 | 93 g (48%) | 94 | 6 |

(a) All reactions were conducted using 100 grams of alcohol that had been previously dried with 3Å molecular sieves and 100 grams of butadiene in a 500 ml 316 s.s. Zipperclave autoclave.
(b) Pd$_2$(dba)3 = tris(dibenzylideneacetone)dipalladium
    4-MP = tris(4-methoxyphenyl)phosphine
(c) Isomeric ratio determined by $C_{13}$ NMR

Hydrogenation of 1-Alkoxy-2,7-octadienes to 1-alkoxy-X-octenes

EXAMPLE 8

A total of 0.5 grams of 5% w Pd on BaSO$_4$ was added to 150 grams (1.07 moles) of a mixture of 95% m 1-methoxy-2,7-octadiene and 5% m 3-methoxy-2,7-octadiene in a drybox. This slurry was transferred to a 500 ml Zipperclave (316 s.s.) autoclave. The reaction mixture was placed under N$_2$ by evacuation and refilling with N$_2$. The reaction mixture was then treated with 1.1 moles of H$_2$ gas at 50 psig H$_2$ pressure at 25° C. over a 18 hour period. The reaction was initially exothermic requiring cold water addition to maintain the temperature at 25–28° C. After the appropriate amount of H$_2$ had been added, the reaction was depressured and sparged with N$_2$.

The contents were filtered using a medium porosity Buchner filter funnel to remove the heterogeneous catalyst. $C_{13}$ NMR indicated that 98% of the terminal olefin had been hydrogenated and that internal double bond was retained, but that the internal double bond had isomerized throughout the chain. Therefore, the isolated product (143 g, 93% of theory) was a mixture of 95% m double bond isomers of 1-methoxyoctene with 5% of the product containing 3-methoxy-3-octene.

Hydroformylation of 1-Alkoxy-Octenes to Alkoxy Nonanols

EXAMPLE 9

A sample of 1-hexoxyoctene obtained from procedures essentially the same as that described in Examples 7 and 8 described previously was hydroformylated as follows: A total of 125.1 grams (0.59 moles) of a mixture of 1-hexoxyoctenes, 20 g of toluene, 1.75 g of a proprietary phosphine ligand and 0.46 grams of cobalt carbonyl was mixed and transferred to a 500 ml 316 s.s. Zipperclave autoclave. The mixture was purged with N$_2$ and then a total of 800 psig of 2/1 H$_2$/CO was added at 25° C. The mixture was heated to 180° C. for 225 minutes. The mixture was then cooled to 25° C. and the gases were purged to achieve atmospheric pressure. The product was distilled to obtain 105 grams of a product with a b.p. of 125° C.–138° C. (0.1 mm Hg). $C_{13}$ NMR confirmed the production of a mixture of linear and branched hexoxynonanols.

EXAMPLE 10

A sample of 1-propoxyoctene obtained from procedures essentially the same as that described in Examples 3 and 8 described previously was hydroformylated as follows: A total of 160 grams (0.94 moles) of a mixture of 1-propoxyoctenes, 25 g of toluene, 3.54 g of a proprietary phosphine ligand and 0.96 grams of cobalt carbonyl was mixed and transferred to a 500 ml 316 s.s. Zipperclave autoclave. The mixture was purged with N$_2$ and then a total of 800 psig of 2/1 H2/CO was added at 25° C. The mixture was heated to 180° C. for 240 minutes. The mixture was then cooled to 25° C. and the gases were purged to achieve atmospheric pressure. The product was distilled to obtain 135 grams of a product with a b.p. of 85° C.–105° C. (0.1 mm Hg). $C_{13}$ NMR confirmed the production of a mixture of linear and branched propoxynonanols.

Alkoxydimerization of Butadiene with Diols—Reaction of Butadiene with 1,3-propanediol—Production of 1-hydroxy-propoxy-2,7-octadiene

EXAMPLE 11

The procedures described in Example 1 were repeated except that a total of 1.03 grams (0.0011 moles) of tris(dibenzylideneacetone) dipalladium and 0.8 g (0.0022 moles) of tris(4-methoxyphenyl)phosphine was dissolved in 103 g (1.35 moles) of dry 1,3-propanediol (previously dried over 3Å molecular sieve) and placed in a 500 ml Zipperclave (316 s.s.) autoclave. The reaction mixture was placed under N$_2$ by evacuation and refilling with N$_2$. The reaction mixture was stirred for 10 minutes at 25° C. in order to dissolve all material. Then the reaction mixture was cooled to −60° C. at which time 100 grams (1.85 moles) of butadiene was transferred to the autoclave from the butadiene feed tank. The reaction mixture was allowed to slowly come to 25° C. with stirring and then heated to 60° C. for 4 hours.

Initially, the reaction was exothermic requiring cold water addition to maintain at 60° C. The reaction was cooled to 25° C. and depressured. The contents were transferred to a separatory funnel and a combination of hexane and water was added. The catalyst was removed by water washing and extraction with salt water. The product mixture was dried over anhydrous sodium sulfate and the product mixture was transferred to a vacuum distillation apparatus. Distillation of the product mixture at 60–80° C. (0.1 mm Hg) afforded 108 g of a mixture of isomers of hydroxypropylenoxyoctadienes. $C_{13}$ NMR confirmed the presence of 97% m 1-hydroxypropyleneoxy-2,7-octadiene and 3% m 3-hydroxypropyleneoxy-2,7-octadiene (both cis and trans isomers). This represents an isolated yield of 56% m basis theoretical product yield.

EXAMPLE 12

Example 11 was repeated exactly except that 0.52 grams (0.00055 moles) of tris(dibenzylideneacetone) dipalladium and 0.4 g (0.0011 moles) of tris(4-methoxyphenyl)phosphine was dissolved in 103 g (1.14 moles) of dry 1,4-butanediol (previously dried over 3Δ molecular sieve) and placed in a 500 ml Zipperclave (316 s.s.) autoclave. Distillation of the product mixture at 110–115° C. (0.1 mm Hg) afforded 108 g of a mixture of isomers of hydroxybutyleneoxyoctadienes. $C_{13}$ NMR confirmed the presence of 94% m 1-hydroxybutyleneoxy-2,7-octadiene and 6% m 3-hydroxybutyleneoxy-2,7-octadiene (both cis and trans isomers). This represents an isolated yield of 48% m basis theoretical product yield.

Hydrogenation of 1-hydroxy-alkoxy-2,7-octadienes to 1-hydroxy-alkoxy octanes

EXAMPLE 13

Hydrogenation of 1-hydroxypropyleneoxy-2,7-octadiene to 3-n-octyloxy-1-propanol

A total of 1 gram of 5% w Pd on $BaSO_4$ was added to 150 grams (0.81 moles) of a mixture of 97% m 1-hydroxypropyleneoxy-2,7-octadiene and 3% m 3-hydroxypropyleneoxy-2,7-octadiene in a drybox. This slurry was transferred to a 500 ml Zipperclave (316 s.s.) autoclave. The reaction mixture was placed under $N_2$ by evacuation and refilling with $N_2$. The reaction mixture was then treated with $H_2$ gas at 300 psig $H_2$ pressure at 25° C. over a 4 hour period. The reaction was initially exothermic requiring cold water addition to maintain the temperature at 25–28° C. After there was no additional drop in $H_2$ pressure, the reaction was depressured and sparged with $N_2$.

The contents were filtered using a medium porosity Buchner filter funnel to remove the heterogeneous catalyst. $C_{13}$ NMR indicated that ~98% of the octadiene had been hydrogenated to octane derivatives. Therefore, the isolated product (145 g, 95% of theory) was a mixture of 97% m 3-n-octyloxy-1-propanol and 3% m 3-(2-ethylhexyloxy)-1-propanol.

Persons of ordinary skill in the art will recognize that many modifications may be made to the foregoing without departing from the spirit and scope thereof. The embodiments described herein are meant to be illustrative only and should not be taken as limiting the invention, which is defined in the following claims.

I claim:

1. A method for producing detergent molecules from butadiene comprising:
    dimerizing and alkoxylating butadiene with primary alkanol in the presence of one or more alkoxy substituted phosphine ligands under alkoxydimerization conditions comprising an alkoxydimerization catalyst, said alkoxydimerization conditions being effective to produce an alkoxydimerization product comprising primarily 1-alkoxy-2,7-octadienes;
    selectively hydrogenating the alkoxydimerization product under selective hydrogenation conditions comprising a hydrogenation catalyst effective to produce a hydrogenation product comprising primarily 1-alkoxy substituted 2-octene; and,
    hydroformylating and reducing said 1-alkoxy substituted 2-octene under hydroxylation conditions effective to produce a product comprising primarily 1-hydroxy-9-alkoxy nonane.

2. The method of claim 1 further comprising selecting said primary alkanol comprising an alkyl group having from about 1 to about 6 carbon atoms.

3. The method of claim 2 wherein said selective hydrogenation conditions comprise a hydrogen:octadiene molar ratio of from about 1:1 to about 1.05:1.

4. The method of claim 3 wherein said selective hydrogenation conditions comprise a selective hydrogenation temperature of from about 0° C. to about 100° C.

5. The method of claim 3 wherein said selective hydrogenation conditions comprise a selective hydrogenation temperature of about 25° C.

6. The method of claim 5 wherein said selective hydrogenation conditions comprise a selective hydrogenation time of about 4 hours or less.

7. The method of claim 6 wherein said selective hydrogenation conditions comprise a selective hydrogenation time of about 1 hour.

8. The method of claim 7 wherein said selective hydrogenation conditions comprise a selective hydrogenation pressure of from about atmospheric pressure to about 10 bar or higher.

9. The method of claim 6 wherein said selective hydrogenation conditions comprise a selective hydrogenation pressure of from about atmospheric pressure to about 10 bar or higher.

10. The method of claim 9 wherein said hydrogenation catalyst comprises palladium.

11. The method of claim 5 wherein said selective hydrogenation conditions comprise a selective hydrogenation time of about 1 hour.

12. The method of claim 3 wherein said alkoxydimerization conditions comprise:
    mixing said alkoxy substituted phosphine ligands with a second primary alkanol effective to produce an alkanol/ligand solution;
    mixing an alkoxydimerization catalyst with said alkanol/ligand solution, producing an alkoxydimerization catalyst mixture;
    subjecting said alkoxydimerization catalyst mixture to activation conditions comprising an activation time and an activation temperature effective to activate said alkoxydimerization catalyst, producing an activated catalyst mixture; and,
    adding an amount of butadiene to said activated catalyst mixture to produce a final alkoxylation/dimerization mixture, and subjecting said final alkoxylation/dimerization mixture to alkoxylation/dimerization conditions effective to alkoxylate and dimerize said butadiene to produce said primarily 1-alkoxy substituted octadiene.

13. The method of claim 12 wherein said alkoxy substituted phosphine ligands are effective to form a product comprising 90 wt. % or more of an intermediate selected from the group consisting of primarily said 1-alkoxy-2,7-octadienes and said 1-hydroxyalkoxy-2,7-octadienes.

14. The method of claim 12 wherein said alkoxy substituted phosphine ligands are alkoxy substituted phenyl phosphine ligands.

15. The method of claim 14 wherein said alkoxydimerization catalyst comprises a noble metal compound which is either soluble or superficially insoluble in said alkanol/ligand solution.

16. The method of claim 15 wherein said noble metal compound comprises two noble metal atoms per molecule.

17. The method of claim 16 wherein:
said activation temperature is about 25° C. or more; and,
said activation time is about 10 minutes.

18. The method of claim 17 wherein the amount of butadiene added is effective to produce a molar ratio of butadiene:alkanol of from about 1:2 to about 1:1.

19. The method of claim 18 further comprising:
cooling said activated catalyst mixture to about −60° C., producing a cooled activated catalyst mixture; and
adding said amount of butadiene to said cooled activated catalyst mixture to produce said final alkoxydimerization mixture.

20. The method of claim 19 wherein said alkoxydimerization conditions comprise:
heating said final alkoxydimerization mixture to a preliminary temperature of about 25° C. or less, producing a preliminary heated final alkoxydimerization mixture; and
heating said preliminary heated final alkoxydimerization to a final alkoxydimerization temperature and maintaining said final alkoxydimerization temperature for a time effective to produce said alkoxydimerization product.

21. The method of claim 20 wherein
said final alkoxydimerization temperature is about 60° C.; and,
said time effective to produce said alkoxydimerization product is about 2 hours or more.

22. The method of claim 21 wherein said time effective to produce said alkoxydimerization product is about 8 hours or less.

23. The method of claim 22 further comprising depressurizing said cooled final alkoxydimerization mixture, producing said alkoxydimerization product.

24. The method of claim 22 wherein said hydrogenation catalyst comprises a heterogeneous fixed bed.

25. The method of claim 24 wherein said alkoxy substituted phenyl phosphine ligands are selected from the group consisting of tris-(2,4,6,trimethoxy phenyl)phosphine and tris-(4-methoxyphenyl)phosphine.

26. The method of claim 25 wherein said alkoxydimerization catalyst is tris(dibenzylideneacetone)dipalladium.

27. The method of claim 24 wherein said alkoxyl substituted phenyl phosphine ligand is tris-(4-methoxyphenyl)phosphine.

28. The method of claim 27 wherein said alkoxydimerization catalyst is tris(dibenzylideneacetone)dipalladium.

29. The method of claim 24 wherein said alkoxydimerization catalyst is tris(dibenzylideneacetone)dipalladium.

30. The method of claim 3 wherein said alkoxy substituted phosphine ligands are effective to form a product comprising 90 wt. % or more of an intermediate selected from the group consisting primarily said 1-alkoxy-2,7-octadienes and said 1-hydroxyalkoxy-2,7-octadienes.

31. The method of claim 3 wherein said alkoxy substituted phosphine ligands are alkoxy substituted phenyl phosphine ligands.

32. The method of claim 3 wherein said alkoxy substituted phenyl phosphine ligands are selected from the group consisting of tris-(2,4,6,trimethoxy phenyl)phosphine and tris-(4-methoxyphenyl)phosphine.

33. The method of claim 3 wherein said alkoxyl substituted phenyl phosphine ligand is tris-(4-methoxyphenyl) phosphine.

34. The method of claim 3 wherein said alkoxydimerization catalyst is tris(dibenzylideneacetone)dipalladium.

35. The method of claim 1 wherein said selective hydrogenation conditions comprise a hydrogen:octadiene molar ratio of from about 1:1 to about 1.05:1.

36. The method of claim 1 wherein said hydrogenation catalyst comprises palladium.

37. The method of claim 1 wherein said hydrogenation catalyst comprises a heterogeneous fixed bed.

38. The method of claim 1 wherein said alkoxy substituted phenyl phosphine ligands are selected from the group consisting of tris-(2,4,6,trimethoxy phenyl)phosphine and tris-(4-methoxyphenyl)phosphine.

39. The method of claim 1 wherein said alkoxyl substituted phenyl phosphine ligand is tris-(4-methoxyphenyl) phosphine.

40. The method of claim 1 wherein said alkoxydimerization catalyst is tris(dibenzylideneacetone)dipalladium.

41. A method for producing detergent molecules from butadiene comprising:
dimerizing and alkoxylating butadiene with primary alkanol comprising an alkyl group having from about 1 to about 6 carbon atoms in the presence of tris-(4-methoxyphenyl)phosphine ligands under alkoxydimerization conditions comprising tris(dibenzylideneacetone)dipalladium catalyst, said alkoxydimerization conditions being effective to produce an alkoxydimerization product comprising primarily 1-alkoxy-2,7-octadienes;
exposing said alkoxydimerization product to selective hydrogenation conditions comprising a hydrogen:octadiene molar ratio of from about 1:1 to about 1.05:1, a selective hydrogenation temperature of about 25° C., a selective hydrogenation time of about 1 hour, a selective hydrogenation pressure of from about atmospheric pressure to about 10 bar or higher, and a heterogeneous fixed bed hydrogenation catalyst, said selective hydrogenation conditions being effective to produce a hydrogenation product comprising primarily 1-alkoxy substituted 2-octene; and,
hydroformylating and reducing said 1-alkoxy substituted 2-octene to produce primarily 1-hydroxy-9-alkoxy nonane.

42. The method of claim 41 wherein said alkoxydimerization conditions comprise:
mixing said tris-(4-methoxyphenyl)phosphine ligands with a second primary alkanol having from about 1 to about 6 carbon atoms to produce an alkanol/ligand solution;

mixing said tris(dibenzylideneacetone)dipalladium catalyst with said alkanol/ligand solution, producing a tris(dibenzylideneacetone) dipalladium catalyst mixture;

subjecting said tris(dibenzylideneacetone) dipalladium catalyst mixture to activation conditions comprising an activation time and an activation temperature effective to activate said tris(dibenzylideneacetone) dipalladium catalyst, producing an activated catalyst mixture; and, adding an amount of butadiene to said activated catalyst mixture to produce a final alkoxylation/dimerization mixture, and subjecting said final alkoxylation/dimerization mixture to alkoxylation/dimerization conditions effective to alkoxylate and dimerize said butadiene to produce said primarily 1-alkoxy-2,7-octadienes.

43. The method of claim 42 wherein:
said activation temperature is about 25° C. or more; and, said activation time is about 10 minutes.

44. The method of claim 43 wherein the amount of butadiene added is effective to produce a molar ratio of butadiene:alkanol of from about 1:2 to about 1:1.

45. The method of claim 44 further comprising:
cooling said activated catalyst mixture to about −24° C., producing a cooled activated catalyst mixture; and
adding said amount of butadiene to said cooled activated catalyst mixture to produce said final alkoxydimerization mixture.

46. The method of claim 45 wherein said alkoxydimerization conditions comprise:
heating said final alkoxydimerization mixture to a preliminary temperature of about 25° C. or less, producing a preliminary heated final alkoxydimerization mixture; and
heating said preliminary heated final alkoxydimerization to a final alkoxydimerization temperature and maintaining said final alkoxydimerization temperature for a time effective to produce said alkoxydimerization product.

47. The method of claim 46 wherein
said final alkoxydimerization temperature is about 60° C.; and,
said time effective to produce said alkoxydimerization product is about 2 hours or more.

48. The method of claim 47 wherein said time effective to produce said alkoxydimerization product is about 8 hours or less.

49. The method of claim 48 further comprising depressurizing said cooled final alkoxydimerization mixture, producing said alkoxydimerization product.

50. A method for producing detergent molecules from butadiene comprising:
dimerizing and alkoxylating butadiene with first and second primary alkanols comprising alkyl groups having a different number of from about 1 to 6 carbon atoms, said dimerizing and alkoxylating occuring in the presence of one or more alkoxy substituted phosphine ligands under alkoxydimerization conditions comprising an alkoxydimerization catalyst, said alkoxydimerization conditions being effective to produce an alkoxydimerization product comprising a blend comprising primarily 1-alkoxy-2,7-octadienes comprising two different alkoxy groups having from about 1 to about 6 carbon atoms;
selectively hydrogenating the alkoxydimerization product under selective hydrogenation conditions comprising a hydrogenation catalyst effective to produce a hydrogenation product comprising a blend comprising primarily 1-alkoxy substituted 2-octenes comprising two different alkoxy groups having from about 1 to about 6 carbon atoms; and,
hydroformylating and reducing said 1-alkoxy substituted 2-octene under hydroxylation conditions effective to produce a blend comprising primarily 1-hydroxy-9-alkoxy nonanes comprising two different alkoxy groups having from about 1 to about 6 carbon atoms.

51. The method of claim 50 wherein said selective hydrogenation conditions comprise a hydrogen:octadiene molar ratio of from about 1:1 to about 1.05:1.

52. The method of claim 51 wherein said selective hydrogenation conditions comprise a selective hydrogenation temperature of from about 0° C. to about 100° C.

53. The method of claim 52 wherein said selective hydrogenation conditions comprise a selective hydrogenation time of about 4 hours or less.

54. The method of claim 53 wherein said hydroxylating said 1-alkoxy substituted 2-octenes comprises hydroformylating said 1-alkoxy substituted 2-octenes and said hydroxylation conditions comprise hydroformylation conditions.

55. The method of claim 53 wherein said alkoxy substituted phenyl phosphine ligands are selected from the group consisting of tris-(2,4,6,trimethoxy phenyl)phosphine and tris-(4-methoxyphenyl)phosphine.

56. The method of claim 53 wherein said alkoxyl substituted phenyl phosphine ligand is tris-(4-methoxyphenyl) phosphine.

57. The method of claim 53 wherein said alkoxydimerization catalyst is tris(dibenzylideneacetone)dipalladium.

58. The method of claim 52 wherein said selective hydrogenation conditions comprise a selective hydrogenation time of about 1 hour.

59. The method of claim 51 wherein said selective hydrogenation conditions comprise a selective hydrogenation temperature of about 25° C.

60. The method of claim 59 wherein said selective hydrogenation conditions comprise a selective hydrogenation time of about 1 hour.

61. The method of claim 60 wherein said selective hydrogenation conditions comprise a selective hydrogenation pressure of from about atmospheric pressure to about 10 bar or higher.

62. The method of claim 61 wherein said hydrogenation catalyst comprises palladium.

63. The method of claim 61 wherein said hydroxylating said 1-alkoxy substituted 2-octenes comprises hydroformylating said 1-alkoxy substituted 2-octenes and said hydroxylation conditions comprise hydroformylation conditions.

64. The method of claim 63 wherein said alkoxydimerization conditions comprise:
mixing said alkoxy substituted phosphine ligands with a third alkanol selected from the group consistion of said first primary alkanol and said second primary alkanol, said third alkanol being effective to produce an alkanol/ligand solution;
mixing an alkoxydimerization catalyst with said alkanol/ligand solution, producing an alkoxydimerization catalyst mixture;
subjecting said alkoxydimerization catalyst mixture to activation conditions comprising an activation time and an activation temperature effective to activate said alkoxydimerization catalyst, producing an activated catalyst mixture; and,
adding an amount of butadiene to said activated catalyst mixture to produce a final alkoxylation/dimerization mixture, and subjecting said final alkoxylation/dimerization mixture to alkoxylation/dimerization conditions effective to alkoxylate and dimerize said butadiene to produce said blend comprising primarily 1-alkoxy-2,7-octadienes comprising two different alkoxy groups having from about 1 to about 6 carbon atoms.

65. The method of claim 61 wherein said alkoxy substituted phosphine ligands are effective to form a product comprising 90 wt. % or more of said blend comprising primarily 1-alkoxy-2,7-octadienes comprising two different alkoxy groups having from about 1 to about 6 carbon atoms.

66. The method of claim 51 wherein said hydroxylating said 1-alkoxy substituted 2-octenes comprises hydroformylating said 1-alkoxy substituted 2-octenes and said hydroxylation conditions comprise hydroformylation conditions.

67. The method of claim 50 wherein said alkoxy substituted phosphine ligands are effective to form a product comprising 90 wt. % or more of said blend comprising primarily 1-alkoxy-2,7-octadienes comprising two different alkoxy groups having from about 1 to about 6 carbon atoms.

68. The method of claim 67 wherein said alkoxy substituted phosphine ligands are alkoxy substituted phenyl phosphine ligands.

69. The method of claim 68 wherein said alkoxydimerization catalyst comprises a noble metal compound which is either soluble or superficially insoluble in said alkanol/ligand solution.

70. The method of claim 69 wherein said noble metal compound comprises two noble metal atoms per molecule.

71. The method of claim 69 wherein:
said activation temperature is about 25° C. or more; and,
said activation time is about 10 minutes.

72. The method of claim 71 wherein the amount of butadiene added is effective to produce a molar ratio of butadiene:alkanol of from about 1:2 to about 1:1.

73. The method of claim 72 further comprising:
cooling said activated catalyst mixture to about −60° C., producing a cooled activated catalyst mixture; and
adding said amount of butadiene to said cooled activated catalyst mixture to produce said final alkoxydimerization mixture.

74. The method of claim 73 wherein said alkoxydimerization conditions comprise:
heating said final alkoxydimerization mixture to a preliminary temperature of about 25° C. or less, producing a preliminary heated final alkoxydimerization mixture; and
heating said preliminary heated final alkoxydimerization to a final alkoxydimerization temperature and maintaining said final alkoxydimerization temperature for a time effective to produce said alkoxydimerization product.

75. The method of claim 74 wherein
said final alkoxydimerization temperature is about 60° C.; and,
said time effective to produce said alkoxydimerization product is about 2 hours or more.

76. The method of claim 75 wherein said time effective to produce said alkoxydimerization product is about 8 hours or less.

77. The method of claim 76 further comprising depressurizing said cooled final alkoxydimerization mixture, producing said alkoxydimerization product.

78. The method of claim 77 wherein said hydrogenation catalyst comprises a heterogeneous fixed bed.

79. The method of claim 78 wherein said alkoxy substituted phenyl phosphine ligands are selected from the group consisting of tris-(2,4,6,trimethoxy phenyl)phosphine and tris-(4-methoxyphenyl)phosphine.

80. The method of claim 78 wherein said alkoxyl substituted phenyl phosphine ligand is tris-(4-methoxyphenyl)phosphine.

81. The method of claim 80 wherein said alkoxydimerization catalyst is tris(dibenzylideneacetone)dipalladium.

82. The method of claim 50 wherein said alkoxy substituted phosphine ligands are alkoxy substituted phenyl phosphine ligands.

83. The method of claim 50 wherein said hydrogenation catalyst comprises a heterogeneous fixed bed.

84. The method of claim 50 wherein said alkoxy substituted phenyl phosphine ligands are selected from the group consisting of tris-(2,4,6,trimethoxy phenyl)phosphine and tris-(4-methoxyphenyl)phosphine.

85. The method of claim 50 wherein said alkoxyl substituted phenyl phosphine ligand is tris-(4-methoxyphenyl)phosphine.

86. The method of claim 50 wherein said alkoxydimerization catalyst is tris(dibenzylideneacetone)dipalladium.

87. A method for producing detergent molecules from butadiene comprising:
dimerizing and alkoxylating butadiene with first and second primary alkanols comprising alkyl groups having a different number of from about 1 to about 6 carbon atoms, said dimerizing and alkoxylating occurring in the presence of tris-(4-methoxyphenyl)phosphine ligands under alkoxydimerization conditions comprising tris(dibenzylideneacetone)dipalladium catalyst, said alkoxydimerization conditions being effective to produce an alkoxydimerization product comprising primarily 1-alkoxy-2,7-octadienes comprising two different alkoxy groups having from about 1 to about 6 carbon atoms;
exposing said alkoxydimerization product to selective hydrogenation conditions comprising a hydrogen:octadiene molar ratio of from about 1:1 to about 1.05:1, a selective hydrogenation temperature of about 25° C., a selective hydrogenation time of about 1 hour, a selective hydrogenation pressure of from about atmospheric pressure to about 10 bar or higher, and a heterogeneous fixed bed hydrogenation catalyst, said selective hydrogenation conditions being effective to produce a hydrogenation product comprising a blend comprising primarily 1-alkoxy substituted 2-octenes comprising two different alkoxy groups having from about 1 to about 6 carbon atoms; and,
hydroformylating and reducing said 1-alkoxy substituted 2-octenes to produce a blend comprising primarily 1-hydroxy-9-alkoxy nonanes-comprising two different alkoxy groups having from about 1 to about 6 carbon atoms.

88. The method of claim 87 wherein said alkoxydimerization conditions comprise:
mixing said tris-(4-methoxyphenyl)phosphine ligands with a third primary alkanol having from about 1 to about 6 carbon atoms to produce an alkanol/ligand solution;
mixing said tris(dibenzylideneacetone)dipalladium catalyst with said alkanol/ligand solution, producing a tris(dibenzylideneacetone) dipalladium catalyst mixture;

subjecting said tris(dibenzylideneacetone) dipalladium catalyst mixture to activation conditions comprising an activation time and an activation temperature effective to activate said tris(dibenzylideneacetone) dipalladium catalyst, producing an activated catalyst mixture; and, adding an amount of butadiene to said activated catalyst mixture to produce a final alkoxylation/dimerization mixture, and subjecting said final alkoxylation/dimerization mixture to alkoxylation/dimerization conditions effective to alkoxylate and dimerize said butadiene to produce said blend comprising primarily 1-alkoxy substituted 2-octenes comprising two different alkoxy groups having from about 1 to about 6 carbon atoms.

89. The method of claim 88 wherein:
said activation temperature is about 25° C. or more; and,
said activation time is about 10 minutes.

90. The method of claim 89 wherein the amount of butadiene added is effective to produce a molar ratio of butadiene:alkanol of from about 1:2 to about 1:1.

91. The method of claim 90 further comprising:
cooling said activated catalyst mixture to about −60°C., producing a cooled activated catalyst mixture; and
adding said amount of butadiene to said cooled activated catalyst mixture to produce said final alkoxydimerization mixture.

92. The method of claim 91 wherein said alkoxydimerization conditions comprise:
heating said final alkoxydimerization mixture to a preliminary temperature of about 25° C. or less, producing a preliminary heated final alkoxydimerization mixture; and
heating said preliminary heated final alkoxydimerization to a final alkoxydimerization temperature and maintaining said final alkoxydimerization temperature for a time effective to produce said alkoxydimerization product.

93. The method of claim 92 wherein
said final alkoxydimerization temperature is about 60° C.; and,
said time effective to produce said alkoxydimerization product is about 2 hours or more.

94. The method of claim 93 wherein said time effective to produce said alkoxydimerization product is about 8 hours or less.

95. The method of claim 94 further comprising depressurizing said cooled final alkoxydimerization mixture, producing said alkoxydimerization product.

* * * * *